US011554131B2

(12) United States Patent
Vigsnæs et al.

(10) Patent No.: US 11,554,131 B2
(45) Date of Patent: Jan. 17, 2023

(54) MIXTURE OF HMOS FOR TREATING AUTOIMMUNE DISEASES

(71) Applicant: Glycom A/S, Hørsholm (DK)

(72) Inventors: Louise Kristine Vigsnæs, Copenhagen (DK); Bruce McConnell, La Tour de Peilz (CH); Kristine Rothaus Christensen, Hillerød (DK)

(73) Assignee: Glycom A/S, Hørsholm (DK)

( * ) Notice: Subject to any disclaimer, the term of this patent is extended or adjusted under 35 U.S.C. 154(b) by 0 days.

(21) Appl. No.: 17/059,942

(22) PCT Filed: May 31, 2019

(86) PCT No.: PCT/IB2019/054522
§ 371 (c)(1),
(2) Date: Nov. 30, 2020

(87) PCT Pub. No.: WO2019/229711
PCT Pub. Date: Dec. 5, 2019

(65) Prior Publication Data
US 2021/0213038 A1    Jul. 15, 2021

(30) Foreign Application Priority Data

May 31, 2018  (DK) ........................... PA 2018 00247
Apr. 9, 2019  (DK) ........................... PA 2019 00444

(51) Int. Cl.
*A61K 31/702* (2006.01)
*A61P 37/02* (2006.01)

(52) U.S. Cl.
CPC ............ *A61K 31/702* (2013.01); *A61P 37/02* (2018.01)

(58) Field of Classification Search
CPC .................................................. A61K 31/702
See application file for complete search history.

(56) References Cited

U.S. PATENT DOCUMENTS

| | | | | |
|---|---|---|---|---|
| 9,217,133 | B2 * | 12/2015 | Sprenger | ................... C12N 1/20 |
| 2012/0171165 | A1 | 7/2012 | Buck et al. | |
| 2016/0243138 | A1 * | 8/2016 | Hennet | .............. A61K 2300/00 |

FOREIGN PATENT DOCUMENTS

| | | |
|---|---|---|
| DK | PA 2018 00247 | 5/2019 |
| DK | PA 2019 00444 | 5/2019 |
| KR | 101773066 B1 | 8/2017 |
| KR | 1017730660000 | 8/2017 |
| WO | 92/11017 A2 | 7/1992 |
| WO | 0104341 A1 | 1/2001 |
| WO | 01/78748 A2 | 10/2001 |
| WO | 2007101862 A1 | 9/2007 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012007588 A9 | 1/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | WO-2013148134 A1 * | 10/2013 ............. A23C 9/206 |
| WO | 2014201037 A2 | 12/2014 |
| WO | WO2017046711 A1 | 3/2017 |
| WO | 2017215722 A1 | 12/2017 |
| WO | 2018006080 A1 | 1/2018 |
| WO | 2019055718 A1 | 3/2019 |
| WO | 2019071021 A2 | 4/2019 |
| WO | 2019087140 A1 | 5/2019 |

OTHER PUBLICATIONS

He, YingYing et al., Gut, "The human milk oligosaccharide 2'-fucosyllactose modulates CD14 expression in human enterocytes, thereby attenuating LPS-induced inflammation", 2016 (first published 2014), vol. 65, pp. 33-46 (Year: 2016).*
Tadasu Urashima et. al., "Milk Oligosaccharides", Copyright © 2011 by Nova Science Publishers, Inc., 2011, pp. 1-99.
Xi Chen, "Human Milk Oligosaccharides (HMOS): Structure, Function, and Enzyme-Catalyzed Synthesis", Advances in Carbohydrate Chemistry and Biochemistry, vol. 72, ISSN 0065-2318, 2015, pp. 113-190.
S. Duranti et al., "Exploration of the Genomic Diversity and Core Genome of the Bifidobacterium adolescentis Phylogenetic Group by Means of a Polyphasic Approach", Applied and Environmental Microbiology, Jan. 2013 vol. 79 No. 1, pp. 336-346.
T. Mandl et al., "Severe intestinal dysbiosis is prevalent in primary Sjögren's syndrome and is associated with systemic disease activity", Arthritis Research & Therapy (2017), 2017, pp. 1-7.
A.W. Campbell, "Autoimmunity and the Gut", Autoimmune Diseases, vol. 2014, Article ID 152428, May 13, 2014, pp. 1-12.

(Continued)

*Primary Examiner* — Bahar Craigo
(74) *Attorney, Agent, or Firm* — Kunzler Bean & Adamson; Tom Briscoe

(57) ABSTRACT

The invention relates to a method, compounds and compositions for the secondary prevention, treatment or dietary management of symptomatic and asymptomatic non-intestinal autoimmune diseases in a non-infant human including Sjogren's syndrome and type 1 diabetes. Said method, compounds and compositions for the secondary prevention, treatment or dietary management include human milk oligosaccharide (HMO), preferably mixtures of human milk oligosaccharides selected from the group of 2'-FL, LNnT, LNT, DFL, and 6'-SL.

20 Claims, 1 Drawing Sheet

(56) References Cited

OTHER PUBLICATIONS

M. Murri et al., "Gut microbiota in children with type 1 diabetes differs from that in healthy children: a case-control study", BMC Medicine, 2013, pp. 1-12.

L. Bode, "Human milk oligosaccharides and their beneficial effects", Division of Neonatology and Division of Gastroenterology and Nutrition, 2013, pp. 515-531.

F. Bottacini, "Diversity, ecology and intestinal function of bifidobacteria", Microbial Cell Factories 2014,, Sep. 4, 2014, pp. 1-15.

R.B. Canani, "Potential beneficial effects of butyrate in intestinal and extraintestinal diseases", World Journal of Gastroenterology, Mar. 28, 2011, vol. 17, Issue 12, pp. 1519-1528.

A. Fasano, "Leaky Gut and Autoimmune Diseases", Clinic Rev Allerg Immunol, Springer Science+Business Media, LLC, Nov. 23, 2011, pp. 71-78.

R.C. Edgar, "UPARSE: highly accurate OTU sequences from microbial amplicon reads", Nature Methods, vol. 10, No. 10, Oct. 2013, pp. 996-1000.

L. Xiao et al., "Early-Life Nutritional Factors and Mucosal Immunity in the Development of Autoimmune Diabetes", Frontiers in Immunology, Sep. 28, 2017, pp. 1-15.

C. Tsigalou et al., "Current insights in Microbiome Shifts in Sjogren's Syndrome and Possible Therapeutic interventions", Frontiers in Immunology, May 24, 2018, pp. 1-7.

M.C. Opazo et al., "Intestinal Microbiota Influences Non-intestinal Related Autoimmune Diseases", Frontiers in Immunology, Mar. 12, 2018, pp. 1-20.

M. Haarman et al., Quantitative Real-Time PCR Assays to Identify and Quantify Fecal Bifidobacterium Species in Infants Receiving a Prebiotic Infant Formula, Applied and Environmental Microbiology, vol. 71, No. 5, May 2005, p. 2318-2324.

A. Hevia et al., "Intestinal Dysbiosis Associated with Systemic Lupus Erythematosus", mBio, ASM, Sep. 30, 2014 vol. 5 Issue 5, pp. 1-10.

A. Klindworth et al., "Evaluation of general 16S ribosomal RNA gene PCR primers for classical and next-generation sequencing-based diversity studies", Nucleic Acids Research, 2013, vol. 41, No. 1, Aug. 28, 2012, pp. 1-11.

European Union Institutions, Bodies, Offices and Agencies, "Commission Notice on the classification of Food for Special Medical Purposes", Official Journal of the European Union, Nov. 25, 2017, pp. C401/1-C401/15.

Ta Van Der Meulen, "The microbiome-systemic diseases connection", Oral Diseases, Mar. 2, 2016, pp. 719-734.

L. Xiao, "Human milk oligosaccharides protect against the development of autoimmune diabetes in NOD-mice", Scientific Reports, Mar. 1, 2018, pp. 1-15.

Tadasu Urashima et. al. "The Predominance of Type I Oligosaccharides Is a Feature Specific to Human Breast Milk1-3", The Glycobiology of Human Milk Oligosaccharides, American Society for Nutrition. Adv. Nutr. 3:, 2012, pp. 473S-782S.

C.A. Autran, "The Therapeutic Potential of Human Milk Oligosaccharides in the Context of Chronic Inflammation", Technische Universitat Muchen, Jan. 24, 2018, pp. 1-171.

E. Elison et al., "Oral supplementation of healthy adults with 2'-O-fucosyllactose and lacto-N-neotetraose is well tolerated and shifts the intestinal microbiota", British JOurnal of Nutrition, Oct. 10, 2016, pp. 1356-1368.

A.P. Vos, "Early Supplementation of Non-Obese Diabetic Mice With Oligosaccharides Isolated From Human Milk Reduces Spontaneous Autoimmune Diabetes Development Later in Life", Gastroenterology, vol. 146 Issue 5, May 2914, AGA Abstracts, Nov. 29, 2017, p. 1.

"Extended European Search Report", EPO, dated Feb. 9, 2022, pp. 1-9.

* cited by examiner

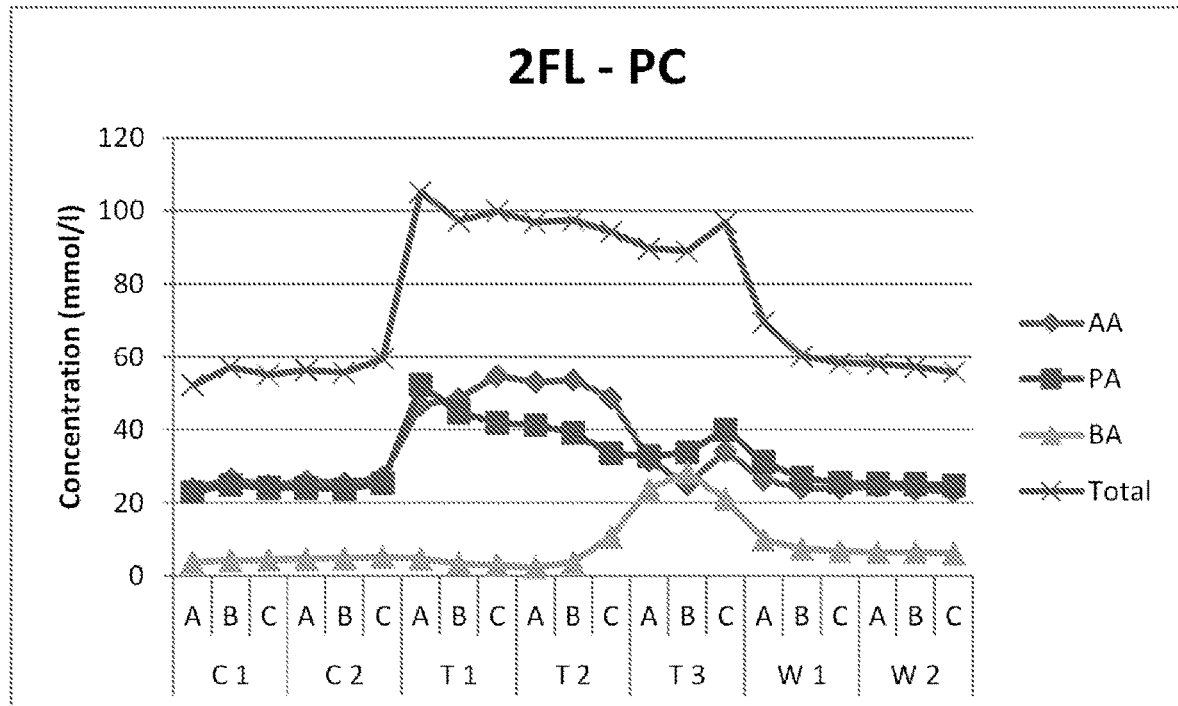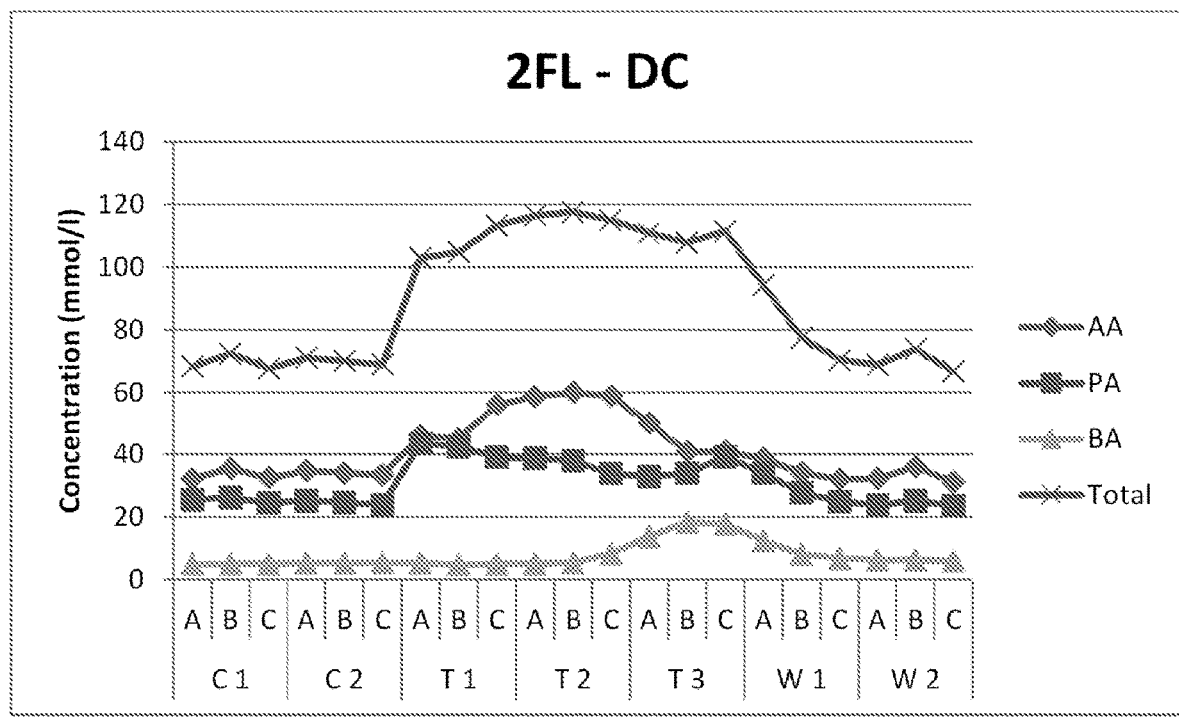

MIXTURE OF HMOS FOR TREATING AUTOIMMUNE DISEASES

CROSS-REFERENCE TO RELATED APPLICATIONS

This application is a National Stage Entry under 35 U.S.C. § 371 of International Application PCT/IB2019/054522 filed on 31 May 2019, which claims priority to Danish Patent Application No. PA 2018 00247 filed 31 May 2018 and to Danish Patent Application PA 2019 00444 filed 9 Apr. 2019, all of which are incorporated herein by reference in their entirety.

FIELD OF THE INVENTION

This invention relates to a method, compounds and compositions for use in dietary management of symptomatic and asymptomatic non-intestinal autoimmune diseases in a non-infant human.

BACKGROUND OF THE INVENTION

Autoimmune diseases are conditions arising from an abnormal immune response to own tissue. They are chronic and reduce quality of life. More than 80 types of autoimmune disorders are known to exist, including both intestinal autoimmune diseases such as Crohn's disease and Coeliac disease, and systemic autoimmune diseases (SAD) such as rheumatoid arthritis, multiple sclerosis, Systemic Lupus Erythematosus, Grave's disease, Hashimoto's thyroiditis, psoriasis, Addison's disease, Sjögren's syndrome, vasculitis, myasthenia gravis, and type I diabetes. Autoimmune diseases are among the leading causes of death among young and middle-aged women in the United States. Incidence rates vary among the autoimmune diseases, with estimates ranging from less than one newly-diagnosed case of systemic sclerosis to more than 20 cases of adult-onset rheumatoid arthritis per 100,000 person-years. At least 85% of systemic sclerosis, systemic lupus erythematosus, and Sjögren's syndrome patients are female. Although most diseases can occur at any age, some diseases primarily occur in childhood and adolescence (e.g. type 1 diabetes), in the mid-adult years (e.g. multiple sclerosis), or among older adults (e.g. Sjögren's syndrome).

The inappropriate immune response against own tissues and molecules results in tissue-specific or systemic inflammation, leading to organ damage and malfunction. The disease progresses from initial naive lymphocyte activation to a chronic state characterized by an increase in the number of autoantigens targeted by T cells and antibodies. Activated autoreactive B cells can function as antigen presenting cells for novel peptides and express co-stimulatory molecules. Antigens are processed and presented to naive T cells leading to the activation of additional autoreactive B cells that present new epitopes up to a point in which there is autoreactivity to a large number of autoantigens. The production of autoantibodies induces damage to tissues by the formation of immune complexes, cytolysis, or phagocytosis of target self-cells and interferes with proper tissue and cellular functions. Although aetiology of autoimmune diseases is unknown, genetic redisposition, environmental factors, and gut microbiota dysbiosis have been identified as possible contributors (Opazo et al. *Front. Microbiol.* 9, 432 (2018)).

It has been estimated that the human intestine harbours $10^{13}$ to $10^{14}$ bacterial cells and the number of bacteria outnumbers the total number of cells in the body by a factor of 10. The microbiota of the human intestine is a complex and very dynamic microbial ecosystem, which is considered to serve numerous essential functions for its human host, including protection against pathogens, induction of immune regulatory functions, nutrient processing and metabolic functions. The composition of the gut microbiota is influenced by numerous factors including diet, antibiotics, microbe-microbe interactions, and host genetics. Changes in these factors can cause microbiota disruption (dysbiosis). Dysbiosis in the human microbiota can have an impact on the gut barrier leading to translocation of bacteria from the lumen to the immunologic compartments of the gut, which can induce local mucosal inflammation and increase intestinal permeability. Pro-inflammatory lymphocytes and cytokines can then spread to the systemic circulation and increase the risk of inflammation at distant anatomical sites, such as the joints, tissues, lacrimal or salivary glands as seen in SAD (Campbell *Autoimmune Dis.* 152428 (2014)).

Several studies have demonstrated association of the intestinal microbiota with SADs such as systemic lupus erythematosus (SLE), Sjögren's syndrome (SS) and type 1 diabetes (T1D). For example, patients with SLE have a lower Firmicutes to Bacteroidetes ratio compared to healthy subjects and a different species composition of *Enterobacteriaceae* (Hevia et al. *mBio.* 5, e01548-14 (2014)). In addition, SS patients have a low relative abundance of beneficial commensal bacteria such as bifidobacteria and *Faecalibacterium prausnitzii* (butyrate-producing bacterium). Additionally, the intestinal dysbiosis in SS patients is associated with clinical markers of systemic disease activity (Mandl et al. *Arthritis Res. Ther.* 19, 237 (2017)). In children with T1D a similar microbiota change has been observed with a decrease of beneficial intestinal bacteria such as *Lactobacillus, Bifidobacterium*, and *Blautia coccoides/Eubacterium rectale* group (group of butyrate-producing bacteria) (Murri et al. *BMC Medicine* 11, 46 (2013)).

Certain members of the intestinal microbiota can produce metabolites such as short chain fatty acids (SCFA), which have distinct physiological effects. SCFAs are produced in the colon by saccharolytic bacteria through fermentation of non-digestible carbohydrates. Their production is influenced by the pattern of food intake and diet-mediated changes in the gut microbiota. The main products are acetate, propionate and butyrate, which are absorbed by the colon. They contribute to shaping of the gut environment, influence the physiology of the colon, and modulate the intestinal immune response. Butyrate acts as the primary energy source for epithelial cells and has been reported to regulate the physical and functional integrity of the colonic mucosa by altering mucin gene and tight junction expression and assembly. In addition, butyrate and propionate have been reported to induce the differentiation of T-regulatory cells, assisting to control intestinal inflammation. This effect is mediated via inhibition of histone deacetylation. Acetate can enhance intestinal defence mediated by epithelial cells and thereby protect the host against assault (Canani et al. *World J. Gastroenterol.* 17, 1519 (2011)).

Dysbiosis in the gut microbiota with decrease abundance of saccharolytic bacteria and butyrate producing bacteria can lead to a reduced production of SCFA, which in turn can impact immune balance in the gut towards inflammation. Gut inflammation has been observed in SAD. For example, increased levels of faecal calprotectin, a validated marker for GI inflammation, has been found in SS patients. An important marker linked to regulation of intestinal permeability and disassembly of tight junction proteins is zonulin.

Deregulation or disruption of the zonulin signalling pathway leads to increased permeability. In T1D patients, high intestinal permeability has been linked to elevated levels of zonulin in the serum. This has also been seen in MS patients (Fasano *Clinic. Rev. Allerg. Immunol.* 42, 71 (2012)).

There is no cure for SAD. Current treatments are focussed on controlling the overactive immune response and bringing down the inflammation. However, they cannot prevent the relapse of symptoms. Treatments include nonsteroidal anti-inflammatory drugs (NSAIDs) such as ibuprofen (Motrin, Advil) and naproxen (Naprosyn) and immune-suppressing drugs such as corticosteroids, calcineurin inhibitors, mTOR inhibitors and IMDH inhibitors.

Recently, biologics targeting specific aspects of the immune system have become treatment options, such as anti-TNFα antibodies (Infliximab). All of these treatments have side effects and their use on a chronic basis is problematic. This has led to the search for treatments better suited to chronic use. Probiotics are one such approach (Opazo et al. *Front. Microbiol.* 9, 432 (2018)). For example, the probiotic mixture VSL3 has been shown to reduce the susceptibility to developing autoimmune diseases in an animal model. However, other probiotics have not given positive results in animal models. Also, evidence of probiotic efficacy in humans is lacking.

Exclusive and prolonged breastfeeding has been identified as a protective factor against the development of type 1 diabetes in humans. This has led to the hypothesis that human milk oligosaccharides (HMOs) may contribute to protecting the infant against development of type 1 diabetes later in life. HMOs are a heterogeneous mixture of soluble glycans found in high concentrations in human milk. This hypothesis has been given substance by work in young NOD-mice showing that a mixture of HMOs extracted from human milk protect against the development of type 1 diabetes in the mice (Xiao et al. *Sci. Rep.* 8, 3829 (2018)). If the results are translatable to humans, administering HMOs to infants and children may offer a way of reducing the risks of type 1 diabetes later in life.

However, there remains a need for safe, well tolerated interventions for the treatment or secondary prevention of SAD in humans.

SUMMARY OF THE INVENTION

A first aspect of the invention relates to a human milk oligosaccharide (HMO), for use in the secondary prevention, treatment or dietary management of a symptomatic and asymptomatic systemic autoimmune disease (SAD) in a non-infant human.

A second aspect of the invention relates to a synthetic composition for use in the secondary prevention, treatment or dietary management of a symptomatic and asymptomatic systemic autoimmune disease (SAD) in a non-infant human, the composition comprising at least one human milk oligosaccharide (HMO).

Preferably, the synthetic composition contains an amount of 1 g to 15 g of the HMO, more preferably 2 g to 10 g. For example, the synthetic composition may contain 3 g to 7 g of the HMO.

A third aspect of the invention is a pack for use in the secondary prevention, treatment or dietary management of a symptomatic and asymptomatic systemic autoimmune disease (SAD) in a non-infant human, the pack comprising at least 14 individual daily doses of an effective amount of at least one human milk oligosaccharide (HMO), advantageously a neutral HMO. Preferably, each dose contains about 1 g to about 15 g of the HMO, more preferably about 2 g to about 10 g. For example, the synthetic composition may contain about 3 g to about 7.5 g of the HMO. Preferably, the pack comprises at least about 21 daily doses, for example about 28 daily doses. The pack can include instructions for use.

The synthetic composition or pack can contain a bifidobacteria, for example *Bifidobacterium longum* and/or *Bifidobacterium bifidum*. The synthetic composition or pack can contain a source of vitamin D. Further, the synthetic composition or pack can contain a source of an omega-3 polyunsaturated fatty acid.

A fourth aspect of the invention relates to a method of secondary prevention, treatment or dietary management of a symptomatic and asymptomatic systemic autoimmune disease (SAD) in a non-infant human, the method comprising administering to the non-infant human an effective amount of at least one human milk oligosaccharide (HMO).

Preferably the non-infant human is administered the HMO for a period of at least 2 weeks, more preferably for at least 3 weeks. For example, the HMO may be administered for 4 weeks or more.

Preferably, the non-infant human is administered an amount of about 1 g to about 15 g per day of the HMO, more preferably about 2 g to about 10 g per day. For example, the non-infant human may be administered about 3 g to about 7.5 g per day. The non-infant human may be administered higher doses during an initial phase and lower doses during a second, maintenance phase. For example, the non-infant human may be administered a treatment dose of about 3 g to about 10 g per day (for example about 4 g to about 7.5 g per day) followed by a maintenance or secondary prevention dose of about 2 g to about 7.5 g per day (for example about 2 g to about 5 g per day).

A fifth aspect of the invention is a use of
one or more human milk oligosaccharides (HMOs),
a synthetic composition comprising one or more human milk oligosaccharides (HMOs), or
a pack comprising at least 14 individual daily doses of an effective amount of one or more human milk oligosaccharides,
in the dietary management of a non-infant human having systemic autoimmune disease (SAD).

In all aspects disclosed above, the HMO can be a neutral HMO or an acidic HMO. The neutral HMO can be one or more fucosylated neutral HMOs or one or more non-fucosylated neutral HMOs. Preferably, the HMO is selected from 2'-FL, 3-FL, DFL, LNT, LNnT, 3'-SL, 6'-SL, LNFP-I or a mixture thereof. Preferably, the HMO comprises one of: 2'-FL and at least one of LNnT and LNT; 2'-FL, DFL and at least one of LNnT and LNT; 2'-FL and 6'-SL; 2'-FL, DFL and 6'-SL; 2'-FL, 6'-SL and at least one of LNnT and LNT; and 2'-FL, DFL, 6'-SL and at least one of LNnT and LNT.

The non-infant SAD patient may suffer from one or more of conditions such as rheumatoid arthritis, multiple sclerosis, Systemic Lupus Erythematosus, Grave's disease, Hashimoto's thyroiditis, psoriasis, psoriatic arthritis, ankylosing spondylitis, Addison's disease, Sjögren's syndrome, vasculitis, myasthenia gravis, and type I diabetes. Further, the non-human infant may additional suffer from one or more of "clouding of consciousness"/"disturbance of consciousness", fatigue, gastrointestinal pain, constipation, diarrhoea, skin rash, anxiety and depression.

In one embodiment, the symptomatic and asymptomatic systemic autoimmune disease (SAD) is Sjögren's syndrome. Preferably, the HMO, also in the synthetic composition and/or the pack according to the invention, comprises, consists essentially of or consists of one or more of 2'-FL, DFL and 6'-SL, like 2'-FL and DFL, 2'-FL and 6'-SL or 2'-FL, DFL and 6'-SL. For example, the Sjögren's syndrome patient may suffer from inflammation of the salivary and/or lacrimal glands.

In another embodiment, the symptomatic and asymptomatic systemic autoimmune disease (SAD) is type 1 diabetes. Preferably, the HMO, also in the synthetic composition and/or the pack according to the invention, comprises, consists essentially of or consists of one or more of 2'-FL, DFL and 6'-SL, like 2'-FL and DFL, 2'-FL and 6'-SL or 2'-FL, DFL and 6'-SL. For example, the type 1 diabetes patient may suffer from insulitis of the pancreas.

Further, the non-infant SAD patient may additionally suffer from one or more of dysbiosis, impaired intestinal barrier function, and gastrointestinal inflammation.

DESCRIPTION OF FIGURES

FIG. 1 presents the absolute values of acetic acid (AA), propionic acid (PA), butyric acid (BA) and total SCFA (total) associated with the 2'-FL treatment in the proximal (PC) and distal (DC) colon reactor. Samples were taken during two control weeks, three treatment weeks and two washout weeks. During each week, three samples (A, B, and C, corresponding to day 1, day 3 and day 5, respectively, in a given week) were collected for metabolic analysis.

DETAILED DESCRIPTION OF THE INVENTION

It has now been surprisingly found that oral or enteral administration of one or more human milk oligosaccharides (HMOs) to humans suffering from systemic autoimmune diseases reduces symptoms of the condition or delays recurrence of relapse. Therefore, human milk oligosaccharides may be used as a treatment, dietary management or secondary prevention of systemic autoimmune diseases in humans. The HMOs also preferentially restore a dysbiotic intestinal microbiota by increasing the abundance of bifidobacteria in the gastro-intestinal tract, in particular bifidobacteria of the *B. adolescentis* phylogenetic group, *Bifidobacterium longum* and/or *Bifidobacterium bifidum*. These bacteria produce lactate and acetate which in turn can be converted into butyrate by butyrate-producing bacteria. In addition, administration of human milk oligosaccharides to non-infant humans preferentially creates a beneficial intestinal microbiota. As an outcome, the gastrointestinal permeability and both intestinal and systemic inflammation is diminished.

The induction of beneficial metabolites such as short chain fatty acids (SCFA) can result in a detectable improvement in one or more indicators or symptoms such as "clouding of consciousness"/"disturbance of consciousness", fatigue, gastrointestinal pain, joint pain, oral and ocular dryness, anxiety, depression and/or skin rash.

Human milk oligosaccharides (HMOs) are a heterogeneous mixture of soluble glycans found in human milk. They are the third most abundant solid component after lactose and lipids in human milk and are present in concentrations of 5-25 g/l (Bode L et al 2013; pp. 515-32. Wageningen Academic Publishers (2013)). HMOs are resistant to enzymatic hydrolysis in the small intestine and are thus largely undigested and unabsorbed and largely reach the colon intact. The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *Bifidobacterium* in the gut of breast-fed infants compared to a more diverse gut microbiota in formula-fed infants. This is viewed as beneficial for the infant because strains of *Bifidobacterium* species are believed to have a positive effect on gut health.

Herein, the following terms have the following meanings:

"Non-infant human" or "non-infant" means a human of 3 years of age and older. A non-infant human can be a child, a teenager, an adult or an elderly person (above 65 years of age).

"Human milk oligosaccharide" or "HMO" means a complex carbohydrate found in human breast milk (Urashima et al.: *Milk Oligosaccharides*. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an αL-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition may be, but preferably is not, identical with a naturally occurring composition. The synthetic composition typically comprises one or more HMOs, that are capable of preferentially increasing the abundance of bifidobacteria, for example *Bifidobacterium longum* and/or *Bifidobacterium bifidum*, in the microbiota of the gastro-intestinal tract and increase the production of butyrate in the gastro-intestinal tract, when administered for a period of about 14 days. In some embodiments the synthetic composition may comprise one or more compounds or components other than HMOs that may have an effect on bifidobacteria or inflammatory tone of a non-infant human subject microbiota in vivo, e.g. non-digestible oligosaccharides or prebiotics, vitamin D and/or omega-3 polyunsaturated fatty acids. Also, in some embodiments, the synthetic compositions may comprise one or more nutritionally or pharmaceutically active components which do not affect adversely the efficacy of the above-mentioned compounds. Some non-limiting embodiments of a synthetic composition of the invention are also described below.

"Microbiota", "microflora" and "microbiome" mean a community of living microorganisms that typically inhabits a bodily organ or part, particularly the gastro-intestinal organs of non-infant humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" means any conventional form for delivery of a composition to a non-infant that causes the deposition of the composition in the gastrointestinal tract (including the stomach). Methods of enteral administration include feeding through a naso-gastric tube or jejunum tube, oral, sublingual and rectal.

"Oral administration" means any conventional form for the delivery of a composition to a non-infant through the mouth. Accordingly, oral administration is a form of enteral administration.

"Effective amount" means an amount of a composition that provides an HMO in a sufficient amount to render a desired treatment outcome in a non-infant human. An effective amount can be administered in one or more doses to achieve the desired treatment outcome.

"Relative abundance of a *Bifidobacterium longum* and/or *Bifidobacterium bifidum*" means the abundance of a *Bifidobacterium longum* and/or *Bifidobacterium bifidum* relative to other bifidobacteria in the microbiota of the gastro-intestinal tract of non-infant humans.

"Relative growth of a *Bifidobacterium longum* and/or *Bifidobacterium bifidum*" means the growth of a *Bifidobacterium longum* and/or *Bifidobacterium bifidum* relative to other bifidobacteria in the microbiota in the gastro-intestinal tract of non-infant humans.

"*Bifidobacterium* of the *B. adolescentis* phylogenetic group" means a bacterium selected from a group consisting of *Bifidobacterium adolescentis, Bifidobacterium angulatum, Bifidobacterium catenulaturn, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:54 (2014)). Preferably a *Bifidobacterium* of the *B. adolescentis* phylogenetic group is *Bifidobacterium* adolescentis and/or *Bifidobacterium pseudocatenulatum*.

"Relative abundance of a *Bifidobacterium* of the *B. adolescentis* phylogenetic group" means the abundance of a *Bifidobacterium* of the *B. adolescentis* phylogenetic group relative to other bifidobacteria in the microbiota of the gastro-intestinal tract of non-infants.

"Relative abundance of *B. adolescentis* and/or *B. pseudocatenulatum*" means the abundance of *B. adolescentis* and/or *B. pseudocatenulatum* relative to other bifidobacteria in the microbiota of the gastro-intestinal tract of non-infants.

"Relative growth of a *Bifidobacterium* of the *B. adolescentis* phylogenetic group" means the growth of a *Bifidobacterium* of the *B. adolescentis* phylogenetic group relative to other bifidobacteria in the microbiota in the gastro-intestinal tract of non-infants.

"Relative growth of *B. adolescentis* and/or *B. pseudocatenulatum*" means the growth of *B. adolescentis* and/or *B. pseudocatenulatum* relative to other bifidobacteria in the microbiota in the gastro-intestinal tract of non-infants.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

"Secondary prevention" means preventing an asymptomatic disease from progressing to symptomatic disease or preventing symptomatic disease for getting worse or reoccurring. In contrast to primary prevention which attempts to prevent the disease or condition from occurring, secondary prevention aims to prevent the disease or condition from getting worse or occurring again. A disease is considered asymptomatic if an individual/patient is a carrier for a disease but experiences no symptoms. A condition might be asymptomatic if it fails to show the noticeable symptoms with which it is usually associated.

Preferably, the invention relates to a dietary management and/or dietary secondary prevention of a symptomatic or asymptomatic SAD in non-infant humans.

The term "dietary management" means exclusive or partial feeding of patients who, because of a disease, disorder or medical condition they are suffering from:
either have a limited, impaired or disturbed capacity to take, digest, absorb, metabolise or excrete ordinary food or certain nutrients contained therein, or metabolites, or
have other medically-determined nutrient requirements
(see: Commission Notice on the classification of Food for Special Medical Purposes of the European Commission, *Official Journal of the European Union C* 401, 25.11.2017, p. 10-11).

In accordance with this invention, it has been discovered that an HMO when administered to non-infant humans suffering from systemic autoimmune diseases reduces symptoms of the disease/condition and/or delays recurrence of relapse. Therefore, human milk oligosaccharides may be used as a treatment, dietary management or secondary prevention of systemic autoimmune diseases in humans. For this reason, an HMO can be used for the treatment or secondary prevention of SAD in non-infant humans. Accordingly, an HMO can be used the treatment and/or secondary prevention of conditions such as rheumatoid arthritis, multiple sclerosis, Systemic Lupus Erythematosus, Grave's disease, Hashimoto's thyroiditis, psoriasis, Addison's disease, Sjögren's syndrome, vasculitis, myasthenia gravis and type I diabetes.

Accordingly, the first aspect of the invention relates to an HMO for the use in the secondary prevention, treatment or dietary management of a symptomatic and asymptomatic systemic autoimmune disease (SAD) in a non-infant human.

The HMO may be one or more fucosylated neutral HMOs, one or more non-fucosylated neutral HMOs, and/or one or more sialylated HMOs. In one embodiment, the HMO is a mixture of neutral HMOs, preferably a mixture comprising, consisting essentially of or consisting of a fucosylated and a non-fucosylated neutral HMO. Particularly, the one or more fucosylated neutral HMO are selected from 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, preferably 2'-FL, 3-FL and DFL. Preferably the one or more non-fucosylated neutral HMOs selected from LNT, LNnT, LNH, LNnH, pLNH and pLNnH, preferably LNnT and LNT. The one or more sialylated HMOs are preferably selected from 3'-SL, 6'-SL, LST a, LST b, LST c, DS-LNT, S-LNH and S-LNnH I, more preferably 3'-SL and 6'-SL. HMOs which contain both fucosylated and sialylated moieties may also be used, for example FSL. In some preferred embodiments, the mixture contains, consists essentially of or consists of i) 2'-FL and/or DFL and ii) LNnT and/or LNT (meaning that the mixture comprises, consists essentially of or consists of at least one of 2'-FL and DFL, and at least one of LNnT and LNT, for example a mixture comprising, consisting essentially of or consisting of 2'-FL and LNnT). The mixture can also contain, consist essentially of or consist of 2'-FL and DFL. In certain embodiment, the mass ratio between i) 2'-FL and/or DFL and ii) LNnT and/or LNT in the mixture is in the range from 5:1 to 1:1, for example the 2'-FL and LNnT ratio in a mixture comprising, consisting essentially of or consisting of 2'-FL and LNnT is 2:1 or 4:1. In other preferred embodiments, the mixture contains, consists essentially of or consists of i) 2'-FL and/or DFL and ii) 3'-SL and/or 6'-SL. These embodiments may also include iii) LNnT and/or LNT.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. Further, WO 01/04341 and WO 2007/101862 describe how to make core human milk oligosaccharides optionally substituted by fucose or sialic acid using genetically modified *E. coli*.

The second aspect of this invention is a synthetic composition comprising a HMO, advantageously a neutral HMO, for use in the secondary prevention, treatment or dietary management of symptomatic and asymptomatic SAD in non-infant humans. The HMO comprised in the synthetic composition is as disclosed in the first aspect.

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the composition can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the gastrointestinal tract.

The pharmaceutical compositions can also include therapeutic agents such as antiviral agents, antibiotics, probiotics, analgesics, and anti-inflammatory agents. The proper dosage of these compositions for a non-infant human can be determined in a conventional manner, based upon factors such as immune status, body weight and age. In some cases, the dosage will be at a concentration similar to that found for the HMO in human breast milk. The required amount would generally be in the range from about 1 g to about 20 g per day, in certain embodiments from about 2 to about 15 g per day, for example from about 3 g to about 7.5 g per day. Appropriate dose regimes can be determined by conventional methods.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the gastrointestinal tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. It is particularly preferred that the composition contains a source of omega-3 polyunsaturated fatty acids; for example fish oil, docosahexaenoic acid, α-Linolenic acid and/or eicosapentaenoic acid. The polyunsaturated fatty acid may also be dihomo-dietary γ-linolenic acid (DGLA).

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron. A source of vitamin D is particularly preferred.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 g/ml of lutein. Lycopene can be included in an amount from about 0.001 μg/ml to about 10 μg/ml, preferably about 0.0185 mg/ml to about 5 g/ml of lycopene. Beta-carotene can comprise from about 0.001 μg/ml to about 10 mg/ml, for example about 0.034 μg/ml to about 5 μg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* sp. *lactic* BB-12, *B. lactis* HN019, *B. lactis* Bi07, *B. infantis* ATCC 15697, *L. rhamnosus* GG, *L. rhamnosus* HNOOI, *L. acidophilus*; LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. The composition can be fed to a non-infant via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

The synthetic composition, preferably the nutritional composition, can also be in a unit dosage form such as a capsule, tablet or sachet/stick pack. For example, the synthetic composition, preferably the nutritional composition, can be in a tablet form or powder form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethylcellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet or stick pack form, can also include various nutrients including macronutrients. Particularly preferred nutrients are a source of vitamin D, omega-3 polyunsaturated fatty acids, and probiotics as described above.

The proper dosage of the HMO or synthetic composition can be determined in a conventional manner, based upon factors such immune status, body weight and age. In some cases, the dosage will be at a concentration similar to that found for the HMOs in human breast milk. The required amount would generally be in the range from about 1 g to about 20 g per day, in certain embodiments from about 1 g to about 15 g per day, for example from about 2 g to about 10 g per day, in certain embodiments from about 3 g to about 7.5 g per day. Appropriate dose regimes can be determined by conventional methods. Ideally, a dose of about 2 g to about 10 g per day is administered with the exact amount selected depending upon whether symptoms are being treated (generally a higher dose) or secondary prevention is intended (lower dose).

The HMO or synthetic composition can be presented in the form of a pack comprising at least 14 individual daily doses of an effective amount of the human milk oligosaccharide. The daily doses are preferably in sachet/stick pack form but may be in any suitable form. Each dose preferably contains about 1 g to about 20 g of the human milk oligosaccharide, more preferably about 2 g to about 15 g, for example about 2 g to about 10 g. Preferably, the pack comprises at least 21 daily doses, more preferably at least 28 daily doses. Most suitable packs contain sufficient for 4 weeks or a full month. The pack can include instructions for use.

An appropriate dose can be determined based on several factors, including, for example, body weight and/or condition, the severity of symptoms, the incidence and/or severity of side effects and the manner of administration. Appropriate dose ranges may be determined by methods known to those skilled in the art. During an initial treatment phase, the dosing can be higher (for example 3 g to 15 g per day, preferably 4 g to 10 g per day, more preferably 4 g to 7.5 g per day). During a maintenance phase, the dosing can be reduced (for example, 1 to 10 g per day, preferably 2 mg to 5 g per day, more preferably 2 g to 5 g per day).

The duration of treatment can be determined based on several factors, including, for example, body weight and/or condition, the severity of symptoms, the incidence and/or severity of side effects. Preferably, the duration is at least 14 days, more preferably at least 3 weeks; even more preferably more than 4 weeks. The synthetic composition or HMOs may also be taken chronically.

The HMOs, synthetic composition and pack can be used in a method for the secondary prevention, treatment or dietary management of a symptomatic and asymptomatic systemic autoimmune disease (SAD) in a non-infant human. The HMOs, synthetic composition and pack are disclosed above.

A certain aspect of the invention is a use of
one or more human milk oligosaccharides (HMOs),
a synthetic composition comprising one or more human milk oligosaccharides (HMOs), or
a pack comprising at least 14 individual daily doses of an effective amount of one or more human milk oligosaccharides,
in the dietary management of a non-infant human having systemic autoimmune disease (SAD). The HMOs, synthetic composition and pack are disclosed above.

EXAMPLES

The working example described herein are for illustration purposes only and should not be considered as limiting.

Example 1

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT by weight, h) 10 g of a 2:1 mixture of 2'-FL and LNnT by weight, and i) 5 g of a 2:1 mixture of 2'-FL and LNnT by weight for 4 weeks. The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 4 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

After 2 weeks, each participant has a visit with the medical team. Faecal samples and blood samples are collected. The faecal samples are stored at −80° C. until analysis. Equipment for new samples are distributed. Subjects are reminded not to change their usual diet during the study.

After 4 weeks, each participant has an exit visit with the medical team. Faecal samples and blood samples are collected. The faecal samples are stored at −80° C. until analysis.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, el (2013)). These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, *Nature Methods* 10, 996 (2013)) is used for bioinformatical analysis of the sequence data.

To assess the *Bifidobacterium* community, ITS profiling of DNA samples is performed.

The results from the profiling of the *Bifidobacterium* community shows that, for the first 2 weeks, the abundance of *B. adolescentis* increases when consuming a single HMO, where the abundance of *B. pseudocatenulatum* increases when consuming a mix of two HMOs. Both *B. adolescentis* and *B. pseudocatenulatum* are members of the *B. adolescentis* phylogenetic group. At 4 weeks, the abundance of members of the *B. adolescentis* phylogenetic group reduce while the abundance of *Bifidobacterium longum* and/or *Bifidobacterium bifidum* increase. It can be seen that oral ingestion of the HMOs for more than 14 days clearly increases the abundance of *Bifidobacterium longum* and/or *Bifidobacterium bifidum* in the microbiota of healthy adults, as well as their relative abundance compared to the totality of other *Bifidobacterium* species. The SCFA analysis indicates that the adults consuming HMO have an initial increase in acetate and propionate followed by and increase in butyrate after about 14 days.

Example 2

The anti-inflammatory effect of HMOs is investigated in the non-obese diabetic (NOD) mouse model of diabetes and Sjögren's Syndrome.

The mice are divided into four groups (n=8) with a control group receiving standard tap water, and the three treatment groups receiving supplementation with 2'-FL, mixture of 2'-FL and DFL (in a 4:1 ratio by weight), or 6'-SL in the drinking water, corresponding to a human daily dose of about 10 grams (calculated by metabolic rate and daily water consumption of NOD mice strains).

The mice receive the treatment for 12 weeks with bi-weekly water changes. From 12 weeks of age, the blood-glucose levels of the mice are checked weekly. Mice with blood-glucose levels above 7 mmol/l are closely monitored and euthanised (and excluded from the study) if their blood glucose levels increase to ≥12 mmol/l on two consecutive measurements.

After 12 weeks treatment the mice are euthanised, and the following are sampled; serum, pancreas, salivary glands, Haarderian lacrimal glands, extraorbital lacrimal glands, as well as caecum and colon content.

The salivary and lacrimal glands are analysed by measuring the total area of inflammatory foci in relation to the total gland size on eight (salivary glands) and two (lacrimal glands) haematoxylin and eosin-stained paraffin-embedded sections per mouse. The pancreas is similarly analysed using histological sections scoring a minimum of 25 (preferably 50) islets of Langerhans for the degree of insulitis with a score ranging from 0-3 (0=no insulitis, 1=peri-insulitis, 2=infiltratory insulitis compromising ≤50% of the islet, 3=infiltratory insulitis compromising ≥50% of the islet).

Caecum content and serum are used to measure the concentration of short chain fatty acids, namely acetate, propionate and butyrate. Faecal samples obtained at baseline together with colon content sampled after euthanasia are used for 16S rRNA genomic sequencing of the microbiota.

Serum samples are also used to measure systemic inflammation by measuring cytokine concentrations using the V-plex Mouse Cytokine 19-Plex Kit from Mesoscale.

The results show that mice treated with 2'-FL, 6'-SL and a mixture of 2'-FL and DFL have reduced inflammation of the salivary and lacrimal glands as well as reduced insulitis of the pancreas compared to the control mice.

Short chain fatty acid measurements show that 2'-FL, and 2'-FL+DFL supplementation increases the acetate concentration in serum when compared to control animals. Treatment with 6'-SL leads to an increase in the concentration of acetate in both caecum and serum, and an increase in the concentration of caecum butyrate.

The data shows that daily supplementation with 2'-FL, 6'-SL or a mixture of 2'-FL and DFL in doses corresponding to a human dose of about 10 g/day reduce inflammation in exocrine glands in NOD mice.

Example 3

The impact of the HMOs on microbiota was investigated in the M-SHIME® (M-TripleSHIME®) in vitro gastrointestinal model (Prodigest). The typical reactor setup of the M-TripleSHIME® consisted of a succession of four reactors simulating the different parts of the human gastrointestinal tract. The first two reactors were of the fill-and-draw principle to simulate different steps in food uptake and digestion, with peristaltic pumps adding a defined amount of SHIME feed (140 ml 3×/day) and pancreatic and bile liquid (60 ml 3×/day), respectively to the stomach and small intestine compartment and emptying the respective reactors after specified intervals. The last two compartments were continuously stirred reactors with constant volume and pH control. The retention time and pH of the different vessels were chosen to resemble in vivo conditions in the different parts of the colon. The proximal colon was set to pH 5.4-5.6 and retention time=12 h, and the distal colon was set to pH 6.0-6.5 and retention time=20 h. 2'-FL, LNnT or Mix (2'-FL:LNnT in 4:1 weight ratio) was added to the SHIME feed in a concentration that equals 10 gram per day.

Upon inoculation with faecal microbiota, these reactors simulated the ascending, transverse and descending colon. After a two-week adaptation of the microbial communities in the different regions of the colon, a representative microbial community was established in the three colon compartments, which differs both in composition and functionality in the different colon regions.

Further, porcine mucin was included in the reactors simulating the colon to take into account the colonisation of the mucous layer. Thus, the M-SHIME® permitted culturing both the luminal and mucous-associated microbial community over periods of several weeks.

The M-SHIME® was run in four stages:
1. Stabilisation: After inoculation of the reactors with a fresh faecal sample taken from a healthy adult, a two-week stabilisation period allowed the microbial community to differentiate in the different reactors depending on the local environmental conditions. During this period the basic nutritional matrix was provided to support the maximum diversity of the gut microbiota originally present in the faecal inoculum.
2. Control: During this two-week period (C1 and C2), a standard nutrient matrix was dosed into the model for a period of 14 days. The baseline microbial community composition and activity in the different reactors was determined by analysis of samples and was used as a reference.
3. Treatment: The SHIME system was operated under normal conditions for 3 weeks (T1, T2 and T3), but with the standard nutrient matrix supplemented with the HMOs. The HMOs tested were 2'-FL, LNnT and a 4:1 mix of 2'-FL and LNnT.
4. Washout: During this two-week period (W1 and W2), the SHIME system is again run with the standard nutrient matrix only.

Samples of the liquids in each reactor were collected regularly (the first, third and fifth day in a week, correspond to A, B, C, respectively, in FIG. 1) and were analysed for microbial metabolites and the composition of the resident microbial community. In particular, the bifidobacteria composition was analysed using ITS profiling.

FIG. 1 presents the absolute values of acetic acid (AA), propionic acid (PA), butyric acid (BA) and total SCFA (total) associated with the 2'-FL treatment in the proximal (PC) and distal (DC) colon reactor.

The results from the fermentation system showed that HMOs impacted the base-acid consumption meaning that HMOs were fermented both in the proximal colon and, to a lesser extent, the distal colon. The bacterial metabolite analysis showed that HMO treatment induced an immediate increase in total SCFA production in both colon regions, mainly due to increase in the production of acetate and propionate. During the third week of HMO treatment, butyrate was increased. This was associated with a decrease in acetate.

The profiling of the *Bifidobacterium* community showed that, for the first 2 weeks (T1 and T2), the abundance of *B. adolescentis* increased when consuming HMOs. However, by week 3 (T3), the relative abundance of members of the *B. adolescentis* phylogenetic group reduced while the abundance and relative abundance of *Bifidobacterium longum* and/or *Bifidobacterium bifidum* increased.

It can be seen that feeding the M-SHIME with HMOs impact the production of SCFA and treatment for more than 14 days increases the concentration of butyrate in both colon regions.

Example 4

A total of 180 male and female participants having a systemic autoimmune condition are recruited to participate in the study. Upon inclusion into the study, each participant completes an electronic survey where they report various gastrointestinal and non-gastrointestinal conditions prior to commencing treatment. A 5 point Likert scale where 1 equals no symptoms and 5 equals severe symptoms is used. Patients then consume about 4 g of either 2'-FL or a 4:1 mix of 2'-FL and LNnT (by weight).

Every 3 weeks thereafter, the patients complete a further survey again reporting various gastrointestinal and non-gastrointestinal conditions. Patients completing the survey are provided with a further 3 week supply of the HMO. Patients not completing the survey are excluded from the study.

After 3 weeks, patients with initial symptoms report improvement in gastrointestinal pain, constipation, diarrhoea, energy levels, ability to concentrate, depression, anxiety and migraine/headache. After 12 weeks, the average symptom scores for the patients drop to levels of the background healthy population. Further, patients without initial symptoms do not show an increase in average symptom scores.

The invention claimed is:
1. A method comprising:
   selecting adult human female with Sjögren's syndrome;
   selecting an amount of one or more synthetic human milk oligosaccharides (HMOs) selected from 2'-FL, DFL, LNnT, LNT, 6'-SL, and combinations thereof, effective for:
   initiating an increase in the relative abundance of *Bifidobacterium adolescentis*; and
   after the increase in the relative abundance of *Bifidobacterium adolescentis* is initiated, increasing the relative abundance of *B. longum* ssp. *longum* and/or *B. bifidum* in the gut microbiota of the adult human female; and reducing the severity and/or frequency of one or more symptoms of the selected autoimmune condition by stimulating an increase in the concentration of colonic acetate and/or propionate and a delayed increase in the concentration of colonic butyrate by administering to the adult human female the effective amount of the selected HMOs.

2. The method according to claim 1, in which the delayed increase in the concentration of colonic butyrate is associated with a decrease in the concentration of colonic acetate.

3. The method according to claim 1, wherein the one or more symptoms of the Sjögren's syndrome are selected from lacrimal gland inflammation, salivary gland inflammation, and combinations thereof.

4. The method according to claim 1, in which the non-infant human is administered a treatment dose of the selected HMOS from about 3 g to about 10 g per day during a treatment period followed by a maintenance dose of from about 2 g to about 5 g per day during a maintenance period.

5. The method according to claim 1, in which the treatment period is at least three weeks.

6. A method comprising:
selecting a non-infant human with a systemic autoimmune disease selected from rheumatoid arthritis, and systemic lupus erythematosus, wherein the non-infant human additionally suffers of one or more of: clouding of consciousness, disturbance of consciousness, fatigue, gastrointestinal pain, skin rash, anxiety, and depression;
selecting an amount of one or more synthetic human milk oligosaccharides (HMOs) selected from 2'-FL, DFL, LNnT, LNT, 6'-SL, and combinations thereof, the selected amount effective for initiating an increase in the relative abundance of *Bifidobacterium adolescentis* and a delayed increase in the relative abundance of *B. longum* ssp. *longum* and/or *B. bifidum* in the gut microbiota of the non-infant human; and
initiating an increase in the relative abundance of *Bifidobacterium adolescentis* and a delayed increase in the relative abundance of *B. longum* ssp. *longum* and/or *B. bifidum* in the gut microbiota of the non-infant human and reducing the severity and/or frequency of symptoms of the systemic autoimmune disease by stimulating an increase in the concentration of colonic acetate and/or propionate and a delayed increase in the concentration of colonic butyrate by administering to the non-infant human an effective amount of the selected HMOs.

7. The method according to claim 6, in which the non-infant human is administered the selected HMOs for a period of at least 3 weeks.

8. The method according to claim 6, in which the non-infant human is administered an amount of from about 1 g to about 15 g per day of the selected HMOs.

9. The method according to claim 6, in which the non-infant human is administered a treatment dose of the selected HMOS from about 3 g to about 10 g per day followed by a maintenance or secondary prevention dose of from about 2 g to about 5 g per day.

10. The method according to claim 6, in which the selected HMOs are a mixture of HMOs selected from:
2'-FL and/or DFL and LNnT and/or LNT;
2'-FL and 6'-SL;
2'-FL, DFL and 6'-SL;
2'-FL, 6'-SL and LNnT and/or LNT; and
2'-FL, DFL, 6'-SL and LNnT and/or LNT.

11. A method comprising:
selecting a non-infant human with a systemic autoimmune disease selected from rheumatoid arthritis, and systemic lupus erythematosus, wherein the non-infant human additionally suffers from one or more of impaired intestinal barrier function, and gastrointestinal inflammation;
selecting an amount of one or more synthetic human milk oligosaccharides (HMOs) selected from 2'-FL, DFL, LNnT, LNT, 6'-SL, and combinations thereof, the selected amount effective for initiating an increase in the relative abundance of *Bifidobacterium adolescentis* and a delayed increase in the relative abundance of *B. longum* ssp. *longum* and/or *B. bifidum* in the gut microbiota of the non-infant human; and
reducing the severity and/or frequency of the one or more symptoms of the systemic autoimmune disease by stimulating an increase in the concentration of colonic acetate and/or propionate and a delayed increase in the concentration of colonic butyrate by administering to the non-infant human an effective amount of the selected HMOs.

12. The method according to claim 11, wherein the non-infant human is administered an amount of from about 1 g to about 15 g per day of the selected HMOs.

13. The method according to claim 11, in which the selected HMOs are a mixture of HMOs selected from:
2'-FL and/or DFL and LNnT and/or LNT;
2'-FL and 6'-SL;
2'-FL, DFL and 6'-SL;
2'-FL, 6'-SL and LNnT and/or LNT; and
2'-FL, DFL, 6'-SL and LNnT and/or LNT.

14. A method comprising:
selecting a non-infant human with multiple sclerosis;
selecting an amount of one or more synthetic human milk oligosaccharides (HMOs) the selected amount effective for initiating an increase in the relative abundance of *Bifidobacterium adolescentis* and a delayed increase in the relative abundance of *B. longum* ssp. *longum* and/or *B. bifidum* in the gut microbiota of the non-infant human; and
reducing the severity and/or frequency of one or more symptoms of the multiple sclerosis by stimulating an increase in the concentration of colonic acetate and/or propionate and a delayed increase in the concentration of colonic butyrate by administering to the non-infant human an effective amount of the selected HMOs.

15. The method according to claim 14, in which selected HMOs are chosen from 2'-FL, DFL, LNnT, LNT, 6'-SL, and combinations thereof.

16. The method according to claim 14, in which the non-infant human is administered the HMOs for a period of at least 3 weeks.

17. The method according to claim 14, in which the non-infant human is administered an amount of from about 1 g to about 15 g per day of the selected HMOs.

18. The method according to claim 17, in which the non-infant human is administered a treatment dose of the selected HMOs from about 3 g to about 10 g per day followed by a maintenance or secondary prevention dose of the selected HMOs of from about 2 g to about 5 g per day.

19. The method according to claim 14, in which the non-infant human additionally suffers from one or more of clouding of consciousness/disturbance of consciousness, fatigue, gastrointestinal pain, skin rash, anxiety and depression.

20. The method according to claim 14, in which the non-infant human additionally suffers from one or more of impaired intestinal barrier function, and gastrointestinal inflammation.

\* \* \* \* \*